United States Patent
Khattar et al.

(10) Patent No.: US 9,872,873 B2
(45) Date of Patent: Jan. 23, 2018

(54) PROCESS FOR PREPARING STABLE PHARMACEUTICAL COMPOSITIONS OF COMPOUNDS SUSCEPTIBLE TO HYDROLYSIS

(75) Inventors: Dhiraj Khattar, Gurgaon (IN); Rajesh Khanna, Gurgaon (IN); Sanjay Motwani, Gurgaon (IN); Minakshi Garg, Gurgaon (IN); Vikas Chandel, Gurgaon (IN); Mukti Yadav, Gurgaon (IN); Vijay Kumar Kyama, Gurgaon (IN); Vikas Bhandari, Gurgaon (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days.

(21) Appl. No.: 14/377,047

(22) PCT Filed: Mar. 29, 2012

(86) PCT No.: PCT/IB2012/051513
§ 371 (c)(1),
(2), (4) Date: Aug. 6, 2014

(87) PCT Pub. No.: WO2013/117969
PCT Pub. Date: Aug. 15, 2013

(65) Prior Publication Data
US 2014/0378407 A1    Dec. 25, 2014

(30) Foreign Application Priority Data
Feb. 6, 2012  (IN) .............................. 337/DEL/2012

(51) Int. Cl.
| | |
|---|---|
| *A61K 31/706* | (2006.01) |
| *A61K 47/02* | (2006.01) |
| *A61K 47/26* | (2006.01) |
| *A61K 31/4184* | (2006.01) |
| *A61K 9/19* | (2006.01) |
| *A61K 9/00* | (2006.01) |

(52) U.S. Cl.
CPC .......... *A61K 31/706* (2013.01); *A61K 9/0019* (2013.01); *A61K 9/19* (2013.01); *A61K 31/4184* (2013.01); *A61K 47/02* (2013.01); *A61K 47/26* (2013.01)

(58) Field of Classification Search
CPC .............. A61K 31/706; A61K 31/4184; A61K 9/0019; A61K 47/02; A61K 47/26
USPC ...................................................... 514/394, 43
See application file for complete search history.

(56) References Cited

U.S. PATENT DOCUMENTS

| | | | |
|---|---|---|---|
| 2006/0069060 A1* | 3/2006 | Redkar | ................. C07H 19/12 514/49 |
| 2011/0042247 A1 | 2/2011 | Kocherlakota et al. | |
| 2014/0142153 A1* | 5/2014 | Kocherlakota | .......... A61K 9/19 514/394 |

FOREIGN PATENT DOCUMENTS

| | | |
|---|---|---|
| CN | 101584670 | 11/2009 |
| WO | 2011/103150 | 8/2011 |

OTHER PUBLICATIONS

Seager et al., "Structure of Products Prepared by Freeze-Drying Solutions Containing Organic Solvents," Journal of Parenteral Science and Technology, vol. 39, No. 4 (1985) pp. 161-179.

\* cited by examiner

*Primary Examiner* — Yih-Horng Shiao
(74) *Attorney, Agent, or Firm* — Occhiuti & Rohlicek LLP

(57) ABSTRACT

The present invention relates to a process of preparing a stable pharmaceutical composition of compounds which are susceptible to hydrolysis comprising a. Addition of required quantity of pharmaceutically acceptable lyophilization excipients optionally in Water for Injection in a formulation vessel; b. Addition of organic solvent to form a appropriate proportion of aqueous and organic solvent; c. Maintaining the temperature of the formulation vessel from the range −5±1° C. to −5±3° C.; d. Addition of required quantity of compound susceptible to hydrolysis to form a solution and lyophilizing the solution.

7 Claims, No Drawings

PROCESS FOR PREPARING STABLE PHARMACEUTICAL COMPOSITIONS OF COMPOUNDS SUSCEPTIBLE TO HYDROLYSIS

CROSS REFERENCE TO RELATED APPLICATIONS

This application is a National Stage of International Application No. PCT/IB2012/051513 filed on Mar. 29, 2012, which claims priority to Indian Application No. 337/DEL/2012 filed Feb. 6, 2012, the contents of which are hereby incorporated by reference in their entirety.

FIELD OF THE INVENTION

The present invention relates to a process for the preparation of stable pharmaceutical compositions of the compounds susceptible to the hydrolytic degradation, using various aqueous or organic solvents or mixture of solvents by Lyophilization at the optimum subzero temperature.

BACKGROUND OF THE INVENTION

Hydrolysis is a chemical process in which a water molecule is added to a substance resulting in the split of that substance into two parts. One fragment of the target molecule (or parent molecule) gains a hydrogen ion (H+) from the split water molecule. The other portion of the target molecule collects the hydroxyl group (OH—) of the split water molecule. In effect an acid and a base are formed.

There are many known compounds which are susceptible to hydrolysis leading to significant degradation of the compounds. Degradation due to hydrolysis leads to difficulty in commercial use of such compounds due to their difficulty in formulating and limiting the impurities under the regulatory specification hence hydrolysis plays an important role in formulating or developing any compound for commercial use.

Azacitidine and Decitabine are chemical analogues of cytidine, a nucleoside present in DNA and RNA. Azacitidine and its deoxy derivative, Decitabine (also known as 5-aza-2' deoxycytidine), are used in the treatment of Myelodysplastic Syndrome. Both drugs were first synthesized in Czechoslovakia as potential chemotherapeutic agents for cancer. Azacitidine belongs to the class of antimetabolites that bear structural similarity to naturally occurring substance, of significance is Cytidine analogs is a pyrimidine nucleosides, generically known as Azacitidine and Decitabine represented by Formula-I & Formula-II respectively, these are antineoplastic agents indicated for the treatment of myelodysplastic syndrome. These analogs of Cytidine have demonstrated significant inhibitory effects on tumor growth in both in vitro and in vivo models.

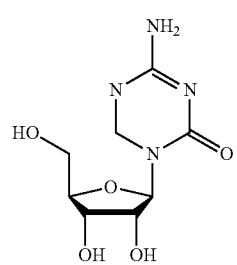

Formula I

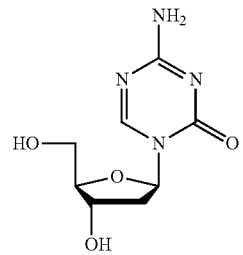

Formula II

Azacitidine acts as a false substrate and potent inhibitor of methyltransferases leading to reduction of DNA methylation affecting the way cell regulation proteins are able to bind to the DNA/RNA substrate However Decitabine is hypomethylating agent, it hypomethylates DNA by inhibiting methyltransferase.

Presently, Azacitidine and Decitabine are marketed as an injectable formulation under the brand name VIDAZA™ and DACOGEN™ respectively, which are available as a sterile lyophilized powder.

Another compound of significance which is susceptible to hydrolytic degradation is Bendamustine chemically known as (4-{5-[Bis(2-chloroethyl)amino]-1-methyl-2-benzimidazolyl}butyric acid, is an atypical structure with a benzimidazole ring, whose structure includes an active nitrogen mustard (see Formula III, which shows Bendamustine Hydrochloride).

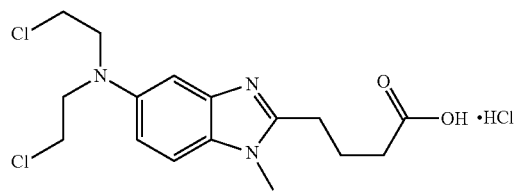

Formula III

Because of their high reactivity in aqueous solutions, nitrogen mustards are difficult to formulate as pharmaceuticals and are often supplied for administration in a lyophilized form that requires reconstitution, usually in water, by skilled hospital personal prior to administration. Once in aqueous solution, nitrogen mustards are subject to degradation by hydrolysis, thus, the reconstituted product should be administered to a patient as soon as possible after its reconstitution.

Bendamustine was initially synthesized in 1963 in the German Democratic Republic (GDR) and was available from 1971 to 1992 in that location under the name Cytostasan®. Since that time, it has been marketed in Germany under the tradename Ribomustin®. It has been widely used in Germany to treat chronic lymphocytic leukemia, Hodgkin's disease, non-Hodgkin's lymphoma, multiple myeloma, and breast cancer.

Bendamustine Hydrochloride is marketed as TREANDA® for Injection is an alkylating drug which is indicated for treatment of patients with Chronic Lymphocytic Leukemia (CLL) and Indolent B-cell non-Hodgkin's lymphoma (NHL) that has progressed during or within six months of treatment with Rituximab or a Rituximab containing regimen.

Due to its degradation in aqueous solutions (like other nitrogen mustards), Bendamustine is supplied as a lyophilized product. The current lyophilized formulation of Bendamustine (Ribomustin®) contains Bendamustine Hydrochloride and Mannitol in a sterile lyophilized powder. The finished lyophilisate is unstable when exposed to light. Therefore, the product is stored in brown or amber-colored glass bottles.

U.S. Pat. No. 4,684,630 discloses a method of parenterally delivering the aqueous-unstable 5-azacytosine arabinoside and 5-Azacitidine compound involving an aqueous dilution of a stable, anhydrous organic solution having the drug dissolved therein. The resulting organic aqueous solution is physiologically suitable for parenteral delivery into warm blooded mammal and contains the drug in an effective dosage concentration per unit volume. The patent discloses the methods of diluting the aqueous unstable anticancer agent with the combination of the aqueous and organic solvents where the preferred organic solvents are Dimethylsulfoxide and Dimethylacetamide.

U.S. Patent Application No. 2006/0159713 relates to the pharmaceutical compositions of lyophilized Bendamustine suitable for pharmaceutical use. According to this patent Application the stability of the Bendamustine is low in aqueous environment hence it has to be administered as soon as possible after reconstitution. This Patent Application reveals the Lyophilized pharmaceutical compositions and discloses the various solvents that can be employed for lyophilization which includes tertiary butanol, n-propanol, n-butanol, isopropanol, ethanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, acetic acid, and cyclohexane. Preferred organic solvents include one or more of ethanol, methanol, propanol, butanol, isopropanol, and tertiary butanol. A more preferred organic solvent is tertiary butanol.

U.S. Patent Application No. 2005/0020615 relates to the Lyophilized CCI-779 formulations composed of CCI-779 and t-butyl alcohol or ethanol.

PCT Application No. WO2011014541 relates to Azacitidine containing compositions that are stable for at least about 24 hours at room temperature, i.e. temperatures of less than or equal to about 25° C. The Patent Application discloses kits containing an amount of Azacitidine or a pharmaceutically acceptable salt thereof, preferably in lyophilized form, in a first vial or container and a pharmacologically suitable fluid which contains at least one of Propylene glycol or Poly Ethylene Glycol, or mixtures thereof and an effective amount of a surfactant, i.e. at least about 0.5%, in a second vial or container. The invention uses the pharmacologically suitable fluids like Propylene glycol or Poly Ethylene Glycol and an effective amount of surfactant and provided as a kit along with lyophilized Azacitidine U.S. Patent Application No. 2011/0042247 relates to the pharmaceutical formulations for parenteral administration comprising Azacitidine or its pharmaceutically acceptable salts and processes for preparing the formulations which includes Lyophilization process. According to the invention the formulation contains the mannitol and water as the ingredients the aqueous solution is prepared at about −3° C. to about −1° C. and then lyophilizing the solution the solvent used here is water and mannitol is used as bulking agent.

The literature reports that VIDAZA™, reconstituted with 4 mL of sterile water for injection to form a suspension for subcutaneous administration, may be stored for up to 1 hour at 25° C. or for up to 8 hours between 2° C. and 8° C. VIDAZA™ reconstituted with 10 mL of sterile water for injection for intravenous administration may be stored at 25° C., but the administration must be completed within 1 hour after reconstitution. The duration of IV infusion administration is limited by the decomposition and instability of Azacitidine, and low aqueous solubility of the drug in aqueous solutions. Further Azacitidine hydrolyzes quickly in water, converting into other forms.

A commercially available product containing Decitabine is sold as Dacogen® by MGI Pharma. The Dacogen® product is for injection and is available as white to almost white lyophilized sterile powder supplied in glass vial. Each 20 mL single dose glass vial contains Decitabine, monobasic potassium phosphate, and sodium hydroxide. Each Dacogen™ vial has to be aseptically reconstituted with 10 mL of sterile water for injection, and upon reconstitution each mL contains approximately 5 mg of Decitabine at pH 6.7-7.3. Immediately after reconstitution, the solution should be further diluted with 0.9% of Sodium Chloride injection, 5% Dextrose Injection, or lactated Ringer injection, to a final concentration of 0.1-1. mg/mL.

The reconstitution of the present commercially available Bendamustine lyophilized powder is difficult. Reports from the clinic indicate that reconstitution can require at least fifteen minutes and may require as long as thirty minutes. Besides being burdensome and time-consuming for the healthcare professional responsible for reconstituting the product, the lengthy exposure of Bendamustine to water during the reconstitution process increases the potential for loss of potency and impurity formation due to the hydrolysis of the product by water.

The manufacture of a freeze dried product necessitates that the product is usually first manufactured as a solution, filtered to sterilize, aseptically filled, and finally lyophilized to remove the solvents. All of these unit operations require that the product be held in the solution state for a defined period of time, at lease for 4 hours. Fabrication of the compounds of the invention in aqueous solution leads to the extensive degradation at 5±3° C.

There exists a need to develop the process of preparing the dosage form of such compounds which can overcome the limitations of the existing processes of manufacturing the finished dosage form such as degradation due to hydrolysis which is the most important aspect of any formulation. The present invention provides advantages in preventing the degradation of the compounds which are susceptible to hydrolysis by using the mixture of aqueous and organic solvent in a particular proportion to depress the freezing point of the solution to a certain level, hence enabling to work at subzero temperatures by maintaining the solubility at that temperature. None of the prior art documents mention the use of the mixture of aqueous and organic solvent to work at subzero temperature i.e. −5±2° C. By using the appropriate combination of the solvents and their concentration degradation of the prelyophized solution can be controlled up to good extent. It was surprisingly found that this process provides the compositions with better degradation profile than the processes for preparation of the compositions for hydrolysis susceptible compounds already known.

SUMMARY OF THE INVENTION

The present invention provides the process for manufacturing stable pharmaceutical compositions of the compounds susceptible to the Hydrolysis. Further aspects of the invention relate to the processes for preparing stable formulations comprising compounds susceptible to Hydrolysis or salts thereof, and method of using the formulation for treating various types of cancer disorders in mammals.

An aspect of the present invention provides processes for preparation of stable pharmaceutical compositions of compounds susceptible to Hydrolysis that may be suitable for Parenteral Administration.

Another aspect of the present invention includes using various organic solvents alone or in combination to bring down the freezing point of the bulk solution during the process of lyophilization to as low as up to −5±2° C. to improve the stability profile of the compounds which are susceptible to hydrolysis.

Another aspect of the present invention is selecting the proper solvent mixture to maintain the satisfactory drug solubility in the solvent system for the compound to be fabricated at sub zero temperature.

Other aspects and advantages of the present invention will be readily apparent from the following detailed description and examples.

DETAILED DESCRIPTION OF THE INVENTION

An aspect of the present invention relate to the process for stable pharmaceutical formulations comprising compounds which are susceptible to Hydrolysis or pharmaceutically acceptable salts thereof. Further aspect of the invention includes the methods of using the formulations for treating various cancerous diseases.

The pharmaceutical formulations as developed by the Inventors of the present invention are provided as Lyophilized Powder that is suitable for Parenteral administration respectively after reconstitution with a suitable diluting fluid.

According to another aspect of the present invention "stability" is referred as to both the physical and chemical stability.

The term "pharmaceutically acceptable" refers to an ingredient that is useful in preparing a pharmaceutical composition that is generally safe, non-toxic, and neither biologically nor otherwise undesirable, and includes those acceptable for veterinary use as well as human pharmaceutical use.

The term "formulation or composition" in accordance with the present invention refers to any of various dosage forms suitable for administration of a drug, such as parenterally, intravenously, intraarterially, intramuscularly, subcutaneously, etc.

As used herein, the term "Pharmaceutically acceptable lyophilization excipient" means the substances optionally used to formulate active pharmaceutical ingredients (API) into pharmaceutical formulations; in a preferred embodiment, an excipient does not lower or interferes with the primary therapeutic effect of the API. Preferably, a pharmaceutically acceptable lyophilization excipient is therapeutically inert. The term "Pharmaceutically acceptable lyophilization excipient" encompasses carriers, diluents, vehicles, solubilizers, stabilizers, pH adjusting agents and bulking agents The "pharmaceutically acceptable lyophilization excipients" can be dissolved in the aqueous phase examples of the useful excipients but are not limited to, mannitol, sodium or potassium dihydrogen phosphate, sucrose, glycerin, dextrose citric acid, tartaric acid, gelatin, and lactose, maltose, dextran, trehalose and sodium hydroxide. Mannitol, sodium or potassium Dihydrogen Phosphate and sodium hydroxide are the preferred pharmaceutically acceptable lyophilization excipients.

The term "organic solvent" means an organic material, usually a liquid, capable of dissolving other substances.

In still another aspect of present invention, the organic solvent is selected from one or more of but not limited to n-propanol, n-butanol, isopropanol, ethanol, methanol, tertiary butanol, dimethyl carbonate, acetone, ethyl acetate, dimethyl sulfoxide, acetonitrile, hexafluoroacetone, chlorobutanol, dimethyl sulfone, acetic acid, and cyclohexane. Preferred organic solvents include one or more of Acetonitrile ethanol, methanol, propanol, butanol, isopropanol. A more preferred organic solvent is Acetonitrile.

Hydrolysis susceptible compounds are those which readily hydrolyze upon coming in contact with the aqueous environment. Examples of such hydrolysis susceptible compounds include, but are not limited to, Anticancer agents, Anti-inflammatory agents, Steroids, Antibiotics, Anti-Infectives, Sedatives and Hypnotics, Alkaloids, etc. Anticancer agents include cytidine analogs and alkylating agents. Cytidine analogs include Azacitidine and Decitabine and Alkylating agents include Bendamustine, Temozolomide and Melphalan.

The term "Azacitidine" is intended to include the free base as well as salts, polymorphs, isomers, enantiomers, hydrates, prodrugs, and any mixtures thereof.

Azacitidine is susceptible to hydrolysis and hydrolyzes quickly in water. In aqueous solution it is attacked by water molecules via nucleophilic reaction as a result of this hydrolytic cleavage, N-Formyl compound hydrolysis product "RGU-CHO" is formed which is reversible reaction and compounds are in equilibrium with each other. This impurity is formed very quickly in aqueous solution. "RGU-CHO" is then later converted to impurity "RGU" by the loss of formic acid which is an irreversible reaction. Degradation of Azacitidine is shown below.

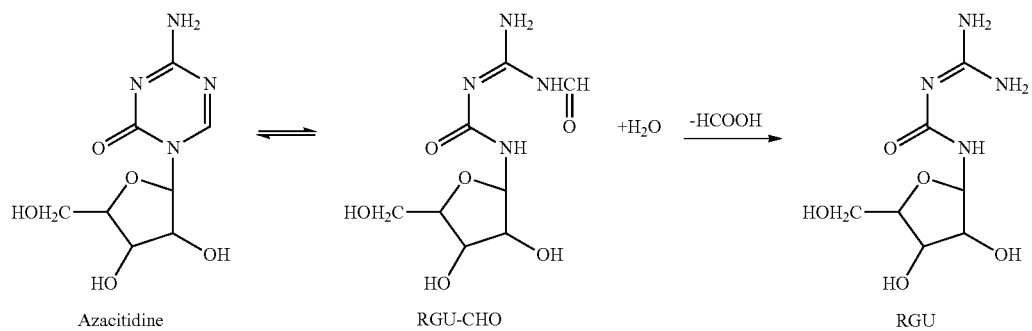

Conversion of Azacitidine to RGU-CHO in water is temperature dependent and directly proportional to temperature. Conversion of RGU-CHO to RGU is temperature and pH dependent. At higher temperature and in acidic and basic conditions (optimal pH for stable formulation is 6-7) formation of RGU is increased.

Azacitidine is prone to thermal degradation in aqueous media therefore it is supplied as sterile lyophilized powder or cake. Manufacture of a sterile lyophilized product necessitates that the product is usually first manufactured as a solution, sterilized by filtration, aseptically filled, and finally lyophilized to remove the solvents. All of these unit operations require that the product be held in the solution state for a defined period of time, at least for 4 hours.

In one embodiment of the invention, a batch of Azacitidine bulk solution was prepared by dissolving the compound (4 mg/mL) and Mannitol (4 mg/mL) in water at room temperature. However, this resulted in significant degradation of the drug within 2 hrs of the drug addition. The results of which are summarized below in Table I.

TABLE I

Solution stability profile of Azacitidine in water at 25° C.

| Time intervals | Results | | | | | |
|---|---|---|---|---|---|---|
| | RGU | Imp-1 | Imp-2 | RGU-CHO | H-Unk | Total Impurity* |
| Initial | 0.164 | 0.027 | 0.051 | 1.158 | ND | 0.078 |
| 1st hour | 0.314 | 0.027 | 0.050 | 6.966 | ND | 0.077 |
| 2nd hour | 0.591 | 0.028 | 0.050 | 10.495 | ND | 0.078 |

*Total impurities excluding RGU & RGU-CHO,
ND—Not detected
H-Unk—Highest Unknown Impurity It is evident from the Table I that Fabrication of the Azacitidine in water at room temperature led to a significant increase in the level of "RGU-CHO" in the Bulk Solution. Further, in order to control the degradation rate of Azacitidine, another batch was manufactured in water at possible temperature i.e. −1° C. to 0° C. by dissolving Azacitidine (4 mg/mL) and Mannitol (4 mg/mL) in water at −1° C. to 0° C. and the solution stability results are shown below in Table II.

TABLE II

Solution stability profile of Azacitidine in water at −1° C. to 0° C.

| Time intervals | Results | | | | | |
|---|---|---|---|---|---|---|
| | RGU | Specified Imp-1 | Specified Imp-2 | RGU-CHO | H-Unk | Total Impurity* |
| Initial | 0.158 | 0.027 | 0.051 | 0.891 | ND | 0.078 |
| 1st hour | 0.175 | 0.025 | 0.051 | 1.767 | ND | 0.076 |
| 2nd hour | 0.166 | 0.025 | 0.051 | 2.283 | ND | 0.076 |
| 3rd hour | 0.175 | 0.026 | 0.051 | 2.921 | ND | 0.077 |
| 4th hour | 0.191 | 0.027 | 0.051 | 4.112 | ND | 0.078 |

*Total impurities excluding RGU & RGU-CHO,
ND—Not detected
H-Unk—Highest Unknown Impurity From the above performed experiments and the results obtained from the experiments clearly shows that even manufacturing at the lower temperature of −1° C. to 0° C. in water resulted in around 4% degradation in "RGU-CHO". Although manufacturing at −1° C. to 0° C. controlled the degradation to some extent, the level of degradation was not acceptable.

The term "Decitabine" is intended to include the free base as well as salts, polymorphs, isomers, enantiomers, hydrates, prodrugs, and any mixtures thereof.

In another aspect of the present invention Decitabine (5-aza-2' deoxycitidine) is an analogue of the natural nucleoside 2'-deoxycytidine. The drug substance is not only sparingly soluble in water but also chemically unstable in aqueous solution. The drug substance undergoes opening of its ring structure in aqueous solution followed by irreversible deformylation and formation of guanylurea derivatives. In aqueous solution, Decitabine (I) is in equilibrium with its ring-open-formylated derivative (II), followed by irreversible deformylation and formation of the guanylurea derivative (III).

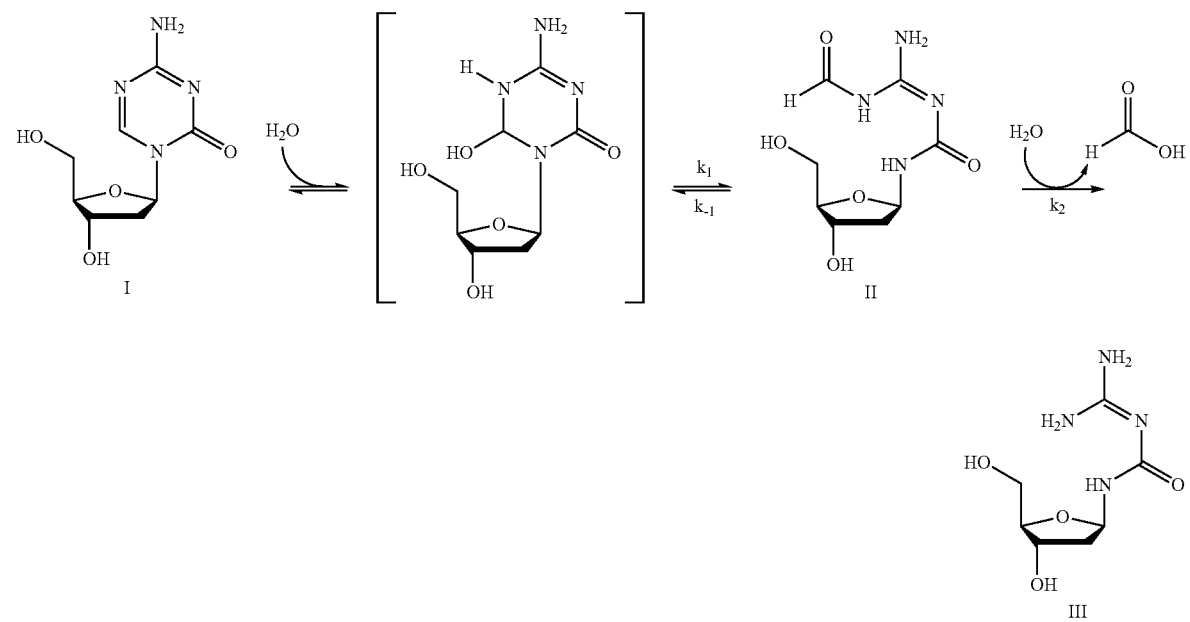

Decitabine is prone to thermal degradation in aqueous media. Therefore, Decitabine is supplied as lyophilized powder and reconstituted with Sterile Water for Injection (SWFI), and diluted in cold infusion fluids prior to administration. Unless used within 15 minutes of reconstitution, the diluted solution must be prepared using cold (2° C.-8° C.) infusion fluids and stored at 2° C.-8° C. (36° F.-46° F.) for up to a maximum of 7 hours until administration.

The manufacture of a freeze dried product necessitates that the product is usually first manufactured as a solution, filtered to sterilize, aseptically filled, and finally lyophilized to remove the solvents. All of these unit operations require that the product be held in the solution state for a defined period of time, at least for 4 hours. A batch of Decitabine bulk solution was prepared by dissolving the drug (5 mg/mL) and buffer (Potassium dihydrogen phosphate 6.8 mg/mL, sodium hydroxide 1.16 mg/mL) in water and at room temperature. However, this resulted in a significant degradation of the drug within 2 hours of drug addition. The stability profile of the Decitabine for injection pre-lyophilized bulk solution at 25° C. is summarized in Table III.

TABLE III

Stability profile of the Decitabine for injection pre-lyophilized bulk solution at 25° C. in water.

| | Related Substances (%) | | | | |
|---|---|---|---|---|---|
| Time | 5-Azacytosine | α-Decitabine | Six member Decitabine | H-unk | Total |
| Initial* | 0.00 | 0.00 | 0.05 | 10.89 | 12.12 |
| 2 h | 0.05 | 0.00 | 0.34 | 12.42 | 25.44 |
| 4 h | 0.05 | 0.00 | 0.81 | 14.14 | 31.46 |

*5 minutes after drug dissolution
H-Unk - Highest Unknown Impurity

From the above table it is evident that fabrication of Decitabine in aqueous solution at room temperature leads to a significant increase in level of impurity in the bulk solution. Even decreasing the temperature of the bulk solution to a level at −1° C. did not solve the degradation problem. In addition, drug solubility in the bulk solution decreased due to lowering of the temperature. The stability profile of the Decitabine for injection pre-lyophilized bulk solution at −1° C. is summarized in Table IV.

TABLE IV

Stability profile of the Decitabine for injection pre-lyophilized bulk solution at −1° C. in water

| | % Related Substances | | | | | | | | |
|---|---|---|---|---|---|---|---|---|---|
| Time | 5-Azacytosine | α-Decitabine | SP1 | SP2 | SP3 | SP4 | SP6 | H-unk | Total |
| Initial* | 0.03 | ND | 0.03 | 0.01 | 0.06 | 0.35 | 0.04 | 0.05 | 0.70 |
| 1 hr | 0.03 | 0.02 | 0.03 | 0.01 | 0.06 | 0.85 | 0.07 | 0.05 | 1.25 |
| 2 hr | 0.04 | 0.02 | 0.03 | 0.02 | 0.05 | 1.50 | 0.22 | 0.05 | 2.06 |
| 3 hr | 0.03 | 0.02 | 0.03 | 0.02 | 0.05 | 2.13 | 0.21 | 0.05 | 2.68 |
| 4 hr | 0.03 | 0.01 | 0.03 | 0.04 | 0.05 | 1.71 | 0.95 | 0.05 | 3.07 |

H-Unk—Highest Unknown Impurity
ND—Not Detected

The term "Bendamustine" is intended to include the free base as well as salts, polymorphs, isomers, enantiomers, hydrates, prodrugs, and any mixtures thereof.

In still another aspect of the present invention in case of Bendamustine it was found that the fabrication of the Bendamustine Hydrochloride in aqueous solution at 5±3° C. leads to a significant increase in the level of impurities in the bulk solution. Stability profile of Bendamustine Hydrochloride for injection pre-lyophilized bulk solution in water (5 mg/mL) at 5±3° C. is summarized in Table V.

TABLE V

Stability profile of Bendamustine Hydrochloride for injection pre-lyophilized bulk solution in water (5 mg/mL) at 5 ± 3° C.

| | % Related Substances | | | | | |
|---|---|---|---|---|---|---|
| Study Condition | Dihydroxy Bendamustine (RRT 0.17) | Monohydroxy Bendamustine (RRT 0.47) | Bendamustine Dimer (RRT 1.23) | Bendamustine Ethyl Ester (BD 5) (RRT 1.38) | H-unk | Total |
| Initial | ND | 0.12 | 0.04 | 0.00 | 0.01 | 0.20 |
| 4 hr | ND | 0.58 | 0.06 | 0.01 | 0.01 | 0.69 |
| 8 hr | ND | 1.59 | 0.10 | 0.01 | 0.01 | 1.77 |
| 24 hr | ND | 4.13 | 0.19 | 0.01 | 0.01 | 4.37 |

H-Unk—Highest Unknown Impurity
ND—Not Detected

Hence to further control the rate and extent of degradation due to hydrolysis it was required to manufacture bulk solution at temperature less than −1° C. The lowest temperature that can be achieved in water with the given formulation is −1° C. to 0° C. To further bring down the manufacturing temperature below −1° C., non-aqueous co-solvent systems have been evaluated for their potential use in the freeze-drying of pharmaceutical products.

TABLE VI

Solubility of Decitabine using various co-solvents at room temperature at various solvent concentrations.

| Solvent | Solubility | | | | | | |
|---|---|---|---|---|---|---|---|
| | 2% | 5% | 10% | 15% | 20% | 30% | 50% |
| Ethanol | Milky dispersion | Milky dispersion | Milky dispersion | Milky dispersion | Milky dispersion | Milky dispersion | Milky dispersion |
| n-Propanol | Milky dispersion | Milky dispersion | Milky dispersion | Milky dispersion | Milky dispersion | Milky dispersion | Milky dispersion |
| n-butanol | Milky dispersion | Milky dispersion | Milky dispersion | Milky dispersion | Milky dispersion | Milky dispersion | Milky dispersion |
| Tertiary-butanol | Milky dispersion | Milky dispersion | Milky dispersion | Milky dispersion | Milky dispersion | Milky dispersion | Milky dispersion |
| Acetonitrile | Clear Solution | Clear solution | Clear solution | Clear solution | Clear solution | Clear solution | Clear solution |

TABLE VII

Freezing point of Bulk solution of Decitabine using various solvents and buffers or their combination

| Solvent | Freezing Point (° C.) | | | | | | |
|---|---|---|---|---|---|---|---|
| | 1% | 2% | 5% | 10% | 15% | 20% | 30% |
| DMSO | −0.5 | −0.8 | −1.6 | −3.0 | −5.5 | −13.9 | −16.0 |
| Ethanol | −0.5 | −0.7 | −2.0 | −2.5 | −6.1 | −13.8 | −14.3 |
| n-butanol | | | | Restricted Miscibility | | | |
| Tertiary-butanol | −0.1 | −1.0 | −2.5 | −4.3 | −6.0 | −9.3 | −12.9 |
| Acetonitrile | — | — | −2 to −3 | −3 to −4 | −4 to −6 | −8 | — |
| 5% DMSO +10% Ethanol + buffer | | | | −5 | | | |
| 5% DMSO + 15% Ethanol + buffer | | | | −6 to −9 | | | |
| 5% DMSO + 10% Ethanol + 20% Tertiary-butanol + buffer | | | | −8 to −10 | | | |

The advantages of using these non-aqueous solvent systems include: increased drug wetting or solubility, increased sublimation rates, increased pre-dried bulk solution or dried product stability, decreased reconstitution time, and enhancement of sterility assurance of the pre-dried bulk solution. A pre-requisite for such a solvent to be utilized efficiently for depression of freezing point of water would be to have satisfactory drug solubility in solvent system. It was found that n-butanol (2-50%), tertiary-butanol (2-50%) were not suitable since the solubility of drug was decreased to an unacceptable level as summarized in Table VI. Various solvents were evaluated for intended purpose e.g. Dimethylsulfoxide (1-30%), Ethanol (1-30%), Tertiary-butanol (1-30%), and their combinations were used in the range of 1-30% and thus were evaluated for their effect in decreasing the freezing point of bulk solution as summarized in Table VII. Although Ethanol decreased the freezing point of the drug solution and ensured drug solubility at low temperature, it was not suitable as a solvent for lyophilization as lyophilized cake could not be formed using this solvent system. Dimethyl sulphoxide is not suitable solvent for Lyophilization as it is difficult to remove during lyophilization.

Surprisingly it was found that the Acetonitrile was found to be only co-solvent that fulfills all the requirements. It was found all of the following advantages could be obtained by use of Acetonitrile-Water system.

1. Acetonitrile depressed the freezing point of water up to −7° C. and thereby making it possible to work at sub-zero temperature range.
2. Increased Drug solubility in Water-Acetonitrile mixture.
3. It was possible to remove Acetonitrile during sublimation and drying step because of its high vapour pressure (72.8 mmHg at 20° C.).
4. Use of Acetonitrile resulted in a good lyophilized cake.

Based on the observations indicating the various advantages of the Acetonitrile over other organic solvents it was selected as the co-solvent in the lyophilization of compounds susceptible to hydrolysis.

In another aspect of the invention the fabrication temperature was controlled at −5±3° C., −5±2° C., −5±1° C. preferably −5±2° C. using Water and Acetonitrile ratio in between 95:5 to 70:30 preferably 80:20 (% v/v) respectively. The hold time data of Azacitidine, Decitabine and Bendamustine obtained in solvent mixture of Water and Acetonitrile at a ratio of 80:20 (% v/v), when fabricated at a temperature range of −5±2° C. is presented in Table VIII, IX, X respectively.

TABLE VIII

Solution stability profile of Water:Acetonitrile 80:20% v/v for Injection formulation of Azacitidine for injection bulk solution at −5 ± 2° C.

| | Results | | | | | | |
|---|---|---|---|---|---|---|---|
| Time intervals | Assay | RGU | Imp-1 | Imp-2 | RGU-CHO | H-Unk | Total Impurity* |
| Initial | 101.80 | 0.143 | 0.05 | 0.068 | 0.164 | ND | 0.118 |
| 1$^{st}$ hour | 101.00 | 0.145 | 0.028 | 0.066 | 0.326 | ND | 0.094 |
| 2$^{nd}$ hour | 101.30 | 0.145 | 0.028 | 0.066 | 0.45 | ND | 0.094 |
| 3$^{rd}$ hour | 100.80 | 0.146 | 0.031 | 0.068 | 0.591 | ND | 0.099 |
| 4$^{th}$ hour | 101.30 | 0.146 | 0.026 | 0.067 | 0.730 | ND | 0.093 |
| 5$^{th}$ hour | 101.00 | 0.148 | 0.049 | 0.069 | 0.839 | ND | 0.118 |

*Total Impurities excluding RGU & RGU-CHO,
ND—Not Detected
H-Unk—Highest Unknown Impurity

TABLE IX

Solution stability profile of Water:Acetonitrile 80:20% v/v formulation of Decitabine for injection bulk solution at −5 ± 2° C.

| | % Related Substances | | | | | | | | | |
|---|---|---|---|---|---|---|---|---|---|---|
| Time | 5-Azacytosine | α-Decitabine | SP1 | SP2 | SP3 | SP4 | SP5 | SP6 | H-unk | Total |
| Initial* | 0.01 | ND | ND | ND | ND | 0.04 | ND | 0.05 | 0.03 | 0.17 |
| 4 hrs | 0.02 | ND | ND | ND | ND | 0.28 | ND | 0.29 | 0.03 | 0.67 |

H-Unk—Highest Unknown Impurity

TABLE X

Solution stability profile of Water:Acetonitrile 80:20% v/v formulation of Bendamustine Hydrochloride for injection bulk solution at −5 ± 2° C.

| | % Related Substances | | | | | |
|---|---|---|---|---|---|---|
| Study Condition | Dihydroxy Bendamustine (RRT 0.17) | Monohydroxy Bendamustine (RRT 0.47) | Bendamustine Dimer (RRT 1.23) | Bendamustine Ethyl Ester (BD 5) (RRT 1.38) | H-unk | Total |
| Initial | ND | 0.01 | 0.05 | 0.003 | 0.03 | 0.15 |
| 1 hr | ND | 0.02 | 0.05 | 0.003 | 0.03 | 0.17 |
| 2 hr | ND | 0.03 | 0.05 | 0.003 | 0.03 | 0.18 |
| 3 hr | ND | 0.04 | 0.05 | 0.003 | 0.03 | 0.19 |
| 6 hr | ND | 0.07 | 0.06 | 0.003 | 0.03 | 0.23 |
| 8 hr | ND | 0.09 | 0.06 | 0.003 | 0.03 | 0.25 |

ND—Not Detected
H-Unk—Highest Unknown Impurity

It is evident from the above summarized data in Table VIII, IX and X the preparation of the prelyophilized solution at −5±2° C. in 80:20% v/v Water/Acetonitrile mixture leads to better initial stability profile with respect to the prelyophilized solution prepared in aqueous solutions at room temperature or even at −1° C. to 8° C.

Hence, Water: Acetonitrile (80:20% v/v) was selected as the final solvent system for preparing the stable Pharmaceutical compositions of hydrolysis susceptible compounds.

In another aspect of the present invention, Lyophilization involves the three steps for drying of the product which include:

1. Freezing the bulk solution
2. Primary drying of the product
3. Secondary drying of the product The Lyophilization cycle parameters for Azacitidine, Decitabine and Bendamustine are summarized in Table XI.

TABLE XI

Lyophilization Cycle parameters for Azacitidine, Decitabine and Bendamustine

| Drug Name | Freezing | Primary Drying | Secondary Drying |
|---|---|---|---|
| Azacitidine | −55° C. for 720 min | −50° C. for 1300 min and −25° C. for 1200 min | 50° C. for 720 min |
| Decitabine | −50° C. for 1635 min | −45° C. to −20° C. for 2950 min | 0° C. to 50° C. for 2950 min |
| Bendamustine | −55° C. for 1650 min | −55 to −17° C. for 2370 min | 0° C. to 50° C. for 2900 min |

The lyophilized products were loaded on stability and were found to be compliant with respect to the proposed specifications.

Certain aspects and embodiments of the invention are further described in following examples, which are provided only for the purposes of illustration and are not intended to limit the scope of the invention in any manner.

Example 1

Azacitidine Pharmaceutical Composition:

| Ingredient | mg/mL |
|---|---|
| Azacitidine | 4.0 mg |
| Mannitol | 4.0 mg |
| Acetonitrile* | 0.2 mL |
| Water for Injection* | q.s. to 1 mL |

*Used as processing aid during manufacturing and removed from the final product during lyophilization Manufacturing Process:
1. Taken about 75% of the required quantity of Water for Injection (WFI) into a formulation vessel.
2. Gradually added and dissolved the required quantity of Mannitol in WFI of step 1 under continuous stirring to get clear solution.
3. Added required quantity of Acetonitrile under continuous stirring.
4. The temperature of the solution was brought down to −5° C.
5. Added required quantity of Azacitidine to the solution of Acetonitrile and Water for Injection under continuous stirring.
6. The temperature of the vessel containing drug was controlled at −5±2° C. throughout the process.
7. Make the volume of the solution to required batch size.
8. Filled the solution into pre-washed and sterilized, glass vials after passing through a second 0.22 μm filter.
9. Subjected the vials through lyophilizing cycle.
10. After Lyophilization is completed, break the vacuum to atmospheric pressure with sterile nitrogen.
11. Stoppered and sealed the vials.

Chemical stability was tested by storing the lyophilized vials under 40±2° C. and 75% relative humidity. Impurity analyses are done before storage ("Initial") and after storage, and are expressed as percentages of the label Azacitidine content. Vials of the commercially available product (VIDAZA®) are similarly stored and analyzed. The comparison of the commercially available Azacitidine (VIDAZA®) and Azacitidine for Injection 100 mg/Vial prepared by using the process of the present invention is summarized in TABLE XII.

| Ingredient | Mg/mL |
|---|---|
| Sodium Hydroxide | 1.16 mg |
| Acetonitrile* | 0.2 mL |
| Water for Injection* | q.s. to 1.0 mL |

*Used as processing aid during manufacturing and removed from the final product during lyophilization Manufacturing Process:
1. Taken about 90% of the required batch quantity of Water for Injection (WFI) into jacketed formulation vessel.
2. Added required quantity of Potassium Dihydrogen Phosphate in WFI.
3. Added required quantity of Sodium Hydroxide in solution.
4. Added 20% of the batch quantity of Acetonitrile to the buffer solution.
5. The temperature was brought down to 0° to −5° C.
6. Taken the remaining quantity of Acetonitrile into separate formulation vessel and lower the temperature to −5°±2° C.
7. Added required quantity of the Decitabine to Acetonitrile of step 6 and mixed to get homogenous solution.
8. Added the buffer solution to the drug dispersion under continuous stirring and maintain the temperature of the vessel at −5°±2° C. throughout the process.
9. The volume of the solution was made to required quantity with WFI.
10. Filtered the solution through 0.22 μm filter.
11. Subjected the vials to the Lyophilization cycle.

TABLE XII

Comparison of the commercially available Azacitidine (VIDAZA ®) and Azacitidine for Injection 100 mg/Vial under 40 ± 2° C. and 75% RH.

| | Azacitidine for Injection 100 mg/Vial | | | | | | VIDAZA ® | | | | | |
|---|---|---|---|---|---|---|---|---|---|---|---|---|
| Study Period | RGU (6.0%) | RGU-CHO (5.0%) | IMP-1 (0.6%) | IMP-2 (0.5%) | H-UNK (0.2%) | T Imp* (2.0%) | Study Period | RGU (6.0%) | RGU-CHO (5.0%) | IMP-1 (0.6%) | IMP-2 (0.5%) | H-UNK (0.2%) | T Imp* (2.0%) |
| Initial | 0.350 | 0.475 | 0.018 | 0.044 | ND | 0.062 | Initial | 2.607 | 1.021 | 0.196 | 0.142 | ND | 0.338 |
| 1 M | 0.383 | 0.232 | 0.015 | 0.028 | ND | 0.043 | 1 M | 2.508 | 0.215 | 0.320 | 0.250 | ND | 0.570 |
| 3 M | 0.805 | 0.158 | 0.043 | 0.080 | ND | 0.123 | 3 M | 2.441 | 0.224 | 0.261 | 0.522 | ND | 0.783 |

*Total Impurities excluding RGU an RGU-CHO
ND—Not detected
H-UNK—Highest Unknown Impurity It is evident from the Example 1 and Table XII that the total Impurities of the lyophilized product obtained by using the lyophilization process using 80:20 Water: Acetonitrile solvent system at −5±2° C. are comparable to the Marketed Composition VIDAZA® and are well within the specified limits.

Example 2

Decitabine Pharmaceutical Composition:

| Ingredient | Mg/mL |
|---|---|
| Decitabine | 5.0 mg |
| Monobasic Potassium Phosphate/Potassium Dihydrogen Phosphate | 6.8 mg |

12. After Lyophilization is complete, break the vacuum to atmospheric pressure with sterile nitrogen.
13. Stoppered and sealed the vials.

Chemical stability was tested by storing the lyophilized vials under 40±2° C. and 75% relative humidity. Impurity analyses are done before storage ("Initial") and after storage, and are expressed as percentages of the label Decitabine content. Vials of the commercially available product (DACOGEN®) are similarly stored and analyzed. The comparison of the commercially available Decitabine (DACOGEN®) and Decitabine for Injection 50 mg/Vial prepared by using the process of the present invention is summarized in TABLE XIII.

TABLE XIII

The comparison of the commercially available Decitabine (DACOGEN ®) and Decitabine for Injection 50 mg/Vial under 40 ± 2° C. and 75% RH

| Related Substances | Decitabine for Injection 50 mg/Vial | | | DACOGEN ® | | |
|---|---|---|---|---|---|---|
| | Initial | 1 Month | 3 Month | Initial | 1 Month | 3 Month |
| 5-Azacytosine | 0.04 | 0.04 | 0.03 | 0.02 | 0.02 | 0.01 |
| α-Decitabine | 0.02 | 0.10 | 0.07 | 0.19 | 0.12 | 0.14 |
| SP-1 | 0.05 | 0.18 | 0.21 | 0.51 | 0.31 | 0.41 |
| SP-2 | 0.21 | 0.08 | 0.08 | 0.17 | 0.12 | 0.14 |
| SP-3 | 0.08 | 0.47 | 0.47 | 0.69 | 0.68 | 0.77 |
| SP-4 | 0.20 | 0.02 | 0.04 | 0.01 | 0.07 | 0.04 |
| SP-5 | 0.10 | ND | 0.02 | 0.00 | — | — |
| SP-6 | 0.20 | 0.03 | 0.02 | 0.03 | — | 0.03 |
| Highest unknown | 0.04 | 0.05 | 0.06 | 0.04 | 0.08 | 0.10 |
| Total | 0.94 | 0.97 | 1.0 | 1.66 | 1.40 | 1.64 |

SP—Specified Impurity
ND—Not Detected

It is evident from the Example 2 and Table XIII that the total Impurities of the lyophilized product obtained by using the lyophilization process using 80:20 Water:Acetonitrile solvent system at −5±2° C. are comparable to the Marketed Composition VIDAZA® and are well within the specified limits.

Example 3

Bendamustine Hydrochloride Pharmaceutical Composition:

| Ingredient | 25 mg/mL/100 mg/mL |
|---|---|
| Bendamustine Hydrochloride | 10.0 mg |
| Mannitol | 17.0 mg |
| Acetonitrile* | 0.2 mL |
| Water* | q.s. to 1 mL |

*Used as processing aid during manufacturing and removed from the final product during lyophilization Manufacturing Process:
1. Taken about 90% of required batch quantity of Water for Injection (WFI) into a formulation vessel.
2. Gradually added and dissolved the batch quantity of Mannitol in WFI of Step 1 and continuously stirred to get a clear solution.
3. Gradually added the batch quantity of Acetonitrile in solution of Step 2 and stirred continuously.
4. The temperature of the solution of Step 3 was brought down to −5°±2° C.
5. Gradually added the required batch quantity of Bendamustine Hydrochloride to the solution of Acetonitrile and Water for Injection (WFI) of Step 4 under continuous stirring.
6. The temperature of the formulation vessel was controlled at −5±2° C.
7. The volume of the solution of Step 6 was made to the required batch size with WFI and stirred to get a uniform solution.
8. Filtered the solution of Step 7 through a 0.22 μm Ultipor N66 filter (M/s Pall) or a suitable equivalent filter in to a pre-autoclaved vessel.
9. Fill the solution into pre-washed and sterilized, glass vials after passing through a second 0.22 μm N66 filter.
10. Partially stoppered the vials during filling.
11. The filled vials were subjected through lyophilizing cycle.
12. After Lyophilization is complete, break the vacuum to atmospheric pressure with sterile nitrogen.
13. The vials were sealed and checked for seal integrity.

Chemical stability was tested by storing the lyophilized vials under 40±2° C. and 75% relative humidity. Impurity analyses are done before storage ("Initial") and after storage, and are expressed as percentages of the label Bendamustine Hydrochloride content. Vials of the commercially available product (TREANDA®) are similarly stored and analyzed.

The comparison of the commercially available Bendamustine Hydrochloride (TREANDA®) and Bendamustine Hydrochloride for Injection 100 mg/Vial prepared by using the process of the present invention is summarized in TABLE XIV.

TABLE XIV

Comparison of the commercially available Bendamustine Hydrochloride (TREANDA ®) and Bendamustine Hydrochloride for Injection 100 mg/Vial under 40 ± 2° C. and 75% RH.

| Related Substances | Bendamustine HCl for Injection 100 mg/Vial | | TREANDA ® | |
|---|---|---|---|---|
| | Initial | 3 M/40° C. | Initial | 3 M/40° C. |
| Dihydroxy Bendamustine (RRT 0.17) | ND | 0.013 | ND | ND |
| Monohydroxy Bendamustine (RRT 0.47) | 0.04 | 0.08 | 0.20 | 0.24 |
| Bendamustine Dimer (RRT 1.23) | 0.06 | 0.20 | 0.41 | 0.64 |
| Bendamustine Ethyl Ester (BD 5) (RRT 1.38) | 0.002 | 0.003 | 0.12 | 0.14 |
| Highest unknown | 0.03 | 0.06 | 0.11 | 0.38 |
| Total | 0.19 | 0.63 | 0.96 | 1.71 |

The comparison of the commercially available Bendamustine Hydrochloride (TREANDA®) and Bendamustine Hydrochloride for Injection 25 mg/Vial prepared by using the process of the present invention is summarized in TABLE XV.

TABLE XV

Comparison of the commercially available Bendamustine Hydrochloride (TREANDA ®) and Bendamustine Hydrochloride for Injection 25 mg/Vial under 40 ± 2° C. and 75% RH.

| Related Substances | Bendamustine HCl for Injection 25 mg/Vial | | TREANDA ® | |
|---|---|---|---|---|
| | Initial | 3 Month/40° C. | Initial | 3 Month/40° C. |
| Dihydroxy Bendamustine (RRT 0.17) | ND | 0.02 | ND | ND |
| Monohydroxy Bendamustine (RRT 0.47) | 0.03 | 0.11 | 0.19 | 0.24 |
| Bendamustine Dimer (RRT 1.23) | 0.07 | 0.27 | 0.16 | 0.36 |

TABLE XV-continued

Comparison of the commercially available Bendamustine Hydrochloride (TREANDA ®) and Bendamustine Hydrochloride for Injection 25 mg/Vial under 40 ± 2° C. and 75% RH.

| Related Substances | Bendamustine HCl for Injection 25 mg/Vial | | TREANDA ® | |
|---|---|---|---|---|
| | Initial | 3 Month/40° C. | Initial | 3 Month/40° C. |
| Bendamustine Ethyl Ester (BD 5) (RRT 1.38) | 0.004 | 0.003 | 0.17 | 0.19 |
| Highest unknown | 0.02 | 0.07 | 0.06 | 0.15 |
| Total | 0.16 | 0.79 | 0.74 | 1.29 |

It is evident from the Example 3 and Table XIV and XV that the total Impurities of the lyophilized product obtained by using the lyophilization process using 80:20 Water: Acetonitrile solvent system at −5±2° C. are comparable to the Marketed Composition TREANDA® and are well within the specified limits.

The invention claimed is:

1. A process of preparing a stable pharmaceutical composition of bendamustine, wherein the process comprises:
   (a) combining a required quantity of a pharmaceutically acceptable lyophilization excipient in water for injection (WFI) with acetonitrile in a formulation vessel to generate a mixture, wherein the proportion of water to acetonitrile in the mixture is 80:20 (v:v);
   (b) maintaining a temperature within the formulation vessel in a range of −5±3° C.;
   (c) adding a required quantity of bendamustine to the formulation vessel in order to form a solution; and
   (d) lyophilizing the solution.

2. The process of claim 1, wherein the pharmaceutically acceptable lyophilization excipient is sodium dihydrogen phosphate, potassium dihydrogen phosphate, mannitol, gelatin, glycerin, dextrose, dextran, citric acid, ascorbic acid, tartaric acid, sodium hydrogen sulfite or sodium hydroxide.

3. The process of claim 2, wherein the pharmaceutically acceptable lyophilization excipient is mannitol, potassium dihydrogen phosphate, sodium dihydrogen phosphate, or sodium hydroxide.

4. The process of claim 1, wherein the temperature within the formulation vessel is −5±2° C.

5. A process of preparing a stable pharmaceutical composition of azacitidine or decitabine wherein the process comprises:
   (a) combining a required quantity of a pharmaceutically acceptable lyophilization excipient in water for injection (WFI) with acetonitrile in a formulation vessel to generate a mixture, wherein the proportion of water to acetonitrile in the mixture is in a ratio of 80:20 (v:v);
   (b) maintaining a temperature within the formulation vessel in a range of −5±2° C.;
   (c) adding a required quantity of azacitidine or decitabine to the formulation vessel in order to form a prelyophilized solution; and
   (d) lyophilizing the solution.

6. The process of claim 1, wherein the process consists of step (a)-step (d).

7. The process of claim 5, wherein the process consists of step (a)-step (d).

* * * * *